(12) United States Patent
Raulerson et al.

(10) Patent No.: US 6,277,100 B1
(45) Date of Patent: *Aug. 21, 2001

(54) CATHETER GUIDE WIRE INTRODUCING DEVICE AND METHOD

(75) Inventors: J. Daniel Raulerson, Brewton, AL (US); Timothy M. Schweikert, Levittown, PA (US)

(73) Assignee: Medical Components, Inc., Harleysville, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/896,192

(22) Filed: Jul. 17, 1997

(51) Int. Cl.$^7$ .................................................. A61M 5/178
(52) U.S. Cl. ................... 604/212; 604/217; 604/167.01; 604/167.03
(58) Field of Search ..................................... 604/164, 167, 604/168, 246, 256, 264, 272, 212, 217, 523, 528, 900, 506, 510, 533, 539; 606/108; 600/581; 128/898

(56) References Cited

U.S. PATENT DOCUMENTS

| | | |
|---|---|---|
| 2,808,967 | 10/1957 | Miller . |
| 4,020,835 * | 5/1977 | Nordstrom et al. ............... 128/214.4 |
| 4,108,175 * | 8/1978 | Orton ................... 128/214.4 |
| 4,652,256 | 3/1987 | Vaillancourt . |
| 4,813,938 | 3/1989 | Raulerson . |
| 4,904,240 | 2/1990 | Hoover . |
| 4,955,871 | 9/1990 | Thomas . |
| 5,009,642 | 4/1991 | Sahi . |
| 5,045,065 | 9/1991 | Raulerson . |
| 5,108,375 | 4/1992 | Harrison et al. . |
| 5,125,903 * | 6/1992 | McLaughlin et al. ............... 604/167 |
| 5,192,284 | 3/1993 | Pleatman . |
| 5,205,828 | 4/1993 | Kedem . |
| 5,269,764 * | 12/1993 | Vetter et al. ......................... 604/167 |
| 5,295,970 | 3/1994 | Clinton et al. . |
| 5,304,156 * | 4/1994 | Sylvanowicz et al. .............. 604/256 |
| 5,334,159 | 8/1994 | Turkel . |
| 5,355,871 | 10/1994 | Hurley et al. . |
| 5,460,616 | 10/1995 | Weinstein et al. . |
| 5,480,388 | 1/1996 | Zadini et al. . |
| 5,492,304 | 2/1996 | Smith et al. . |
| 5,501,671 | 3/1996 | Rosen et al. . |

* cited by examiner

*Primary Examiner*—Richard K. Seidel
*Assistant Examiner*—Michael J Hayes
(74) *Attorney, Agent, or Firm*—Akin, Gump, Strauss, Hauer & Feld, L.L.P.

(57) ABSTRACT

A catheter guide wire introducing device for aspiration of a body part and insertion of a guide wire into the body part is provided. The catheter guide wire introducing device includes a flexible bulb. A fitting is located on the first end of the bulb. The fitting includes an internal chamber and first and second axially aligned passageways in fluid communication with the chamber. A third passageway is provided in fluid communication between the chamber and the interior of the cavity of the flexible bulb. An introducer needle having first and second ends and a lumen is provided. The first end of the needle is connected to the fitting such that the first passageway is in fluid communication with the lumen. A conduit having first and second ends and a passageway extending therethrough is also provided. The conduit is axially aligned with the introducer needle. The first end of the conduit is connected to the fitting such that the conduit passageway is in fluid communication with the second passageway. The conduit and the introducer needle are axially aligned. A guide wire penetrable seal assembly is connected to the second end of the conduit in fluid communication with the conduit passageway for preventing the passage of fluid from within the conduit and air from outside the conduit therethrough and for introduction of the guide wire into the conduit.

16 Claims, 2 Drawing Sheets

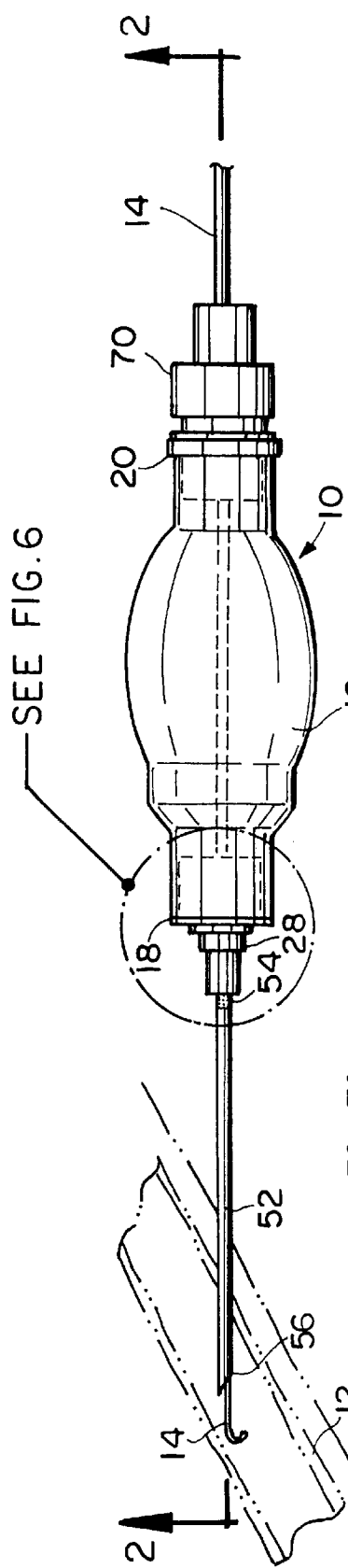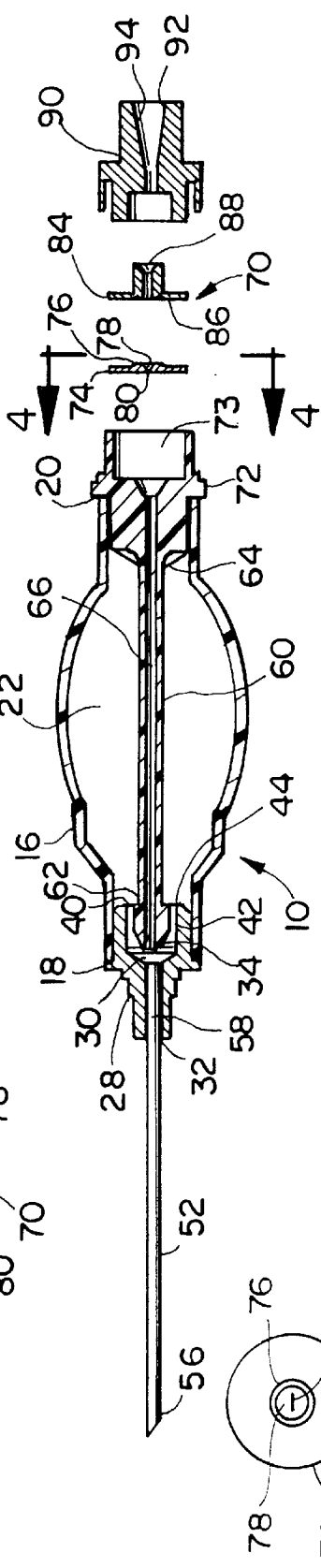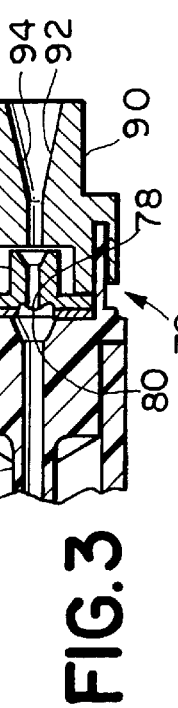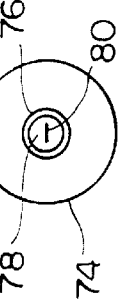

CATHETER GUIDE WIRE INTRODUCING DEVICE AND METHOD

BACKGROUND OF THE INVENTION

Catheters for the introduction or removal of fluids may be located in various venous locations and cavities throughout the body for introducing or removing fluids. Such catheterization may be performed by using a single catheter having multiple lumens. A typical example of a multiple lumen catheter is a dual lumen catheter in which one lumen introduces fluids and one lumen removes fluids. Catheterization may also be performed by using separate, single lumen catheters inserted through two different incisions into an area to be catheterized. Such multiple catheter assemblies are known as Tesio catheters.

Generally, to insert any catheter in a blood vessel, the vessel is identified by aspiration using an introducer device, such as a syringe having a long hollow needle in accordance with the Seldinger technique. Generally, a needle is attached to a syringe and inserted under the patient's skin, with the plunger being withdrawn as the needle is inserted. When blood enters the syringe attached to the needle, indicating that the vessel has been found, the syringe body is removed and a thin guide wire is introduced through the needle lumen and into the interior of the vessel. The needle is then removed leaving a portion of the guide wire within the vessel and the remainder projecting outwardly to a point beyond the surface of the patient's skin. Other guide wire introducing devices and syringes are also available as discussed below. At this point, the catheter is inserted by the physician over the guide wire using one of several known techniques.

In the case of single-lumen catheters typically used in multiple catheter assemblies (e.g., a Tesio catheter), a physician may use an introducer sheath. If a Tesio catheter is used for hemodialysis, for example, each catheter may be inserted in two separate veins. Alternatively, each catheter may be inserted in two different locations of the same vein, such as the internal jugular vein or in a single insertion site as described in U.S. Pat. No. 5,624,413. The introducer sheath is simply a large, stiff, thin-walled tube which serves as a temporary conduit for the permanent catheter which is being placed. The introducer sheath is positioned by placing a dilator device inside of the introducer and passing both the dilator and the introducer together into the vessel over the guide wire. The guide wire, which is partially within the vessel after insertion as described above, and the dilator are then removed, leaving the thin-walled introducer sheath in place. The catheter is placed through the introducer sheath.

In each case, the first step is aspirating the vessel or area to be catheterized prior to introducing the guide wire. This is often troublesome, especially when aspirating blood vessels, due to the flashback of blood. Arterial blood may spurt from the needle insertion point with considerable force and may contact a physician or other attendant assisting the physician, causing the risk of contamination with blood borne pathogens, such as HIV virus or hepatitis. While some known devices attempt to address this problem by providing a blood reservoir to collect such flashback blood, they do not provide any positive means for controllably drawing blood into the reservoir. In other known devices, blood can be controllably drawn into a reservoir by a plunger with a syringe-type device. However, such devices require two hands to operate.

A second problem which is of greater concern to the patient is exposing certain venous blood vessels or other body cavities to atmospheric pressure. Veins are often under negative pressure as blood is being drawn back to the thoracic cavity due to the process of inspiration during the breathing cycle, and a hole in a venous blood vessel could lead to air being drawn into the blood vessel, creating an air embolism.

In other types of catheterization procedures, such as a pleural effusion where fluid which collects around the lungs is drained, it is important to have a closed system guide wire introduction device which prevents atmospheric air from entering the thoracic cavity. Breathing movement creates negative pressure in the thoracic cavity which, in combination with the air in the lungs, keeps the lungs expanded. The introduction of air into the thoracic cavity could cause the lungs to partially collapse. It is therefore important during the insertion of a guide wire for catheterization that the risk of introducing air into the thoracic cavity or a vessel be minimized.

There is a need in the art for a closed system catheter guide wire introducing device which can be used with one hand and which minimizes the risk of contamination by blood borne pathogens as well as reducing the risk of the introduction of air into a body cavity or an air embolism.

BRIEF SUMMARY OF THE INVENTION

Briefly stated, the present invention provides a catheter guide wire introducing device for aspiration of a body part and insertion of a guide wire into the body part. The catheter guide wire introducing device comprises a flexible bulb having a first end, a closed second end and an interior cavity. A fitting is located on the first end of the bulb. The fitting includes an internal chamber and first and second axially aligned passageways in fluid communication with the chamber. A third passageway is provided in fluid communication between the chamber and the interior of the cavity of the flexible bulb. An introducer needle having first and second ends and a lumen is provided. The first end of the needle is connected to the fitting such that the first passageway is in fluid communication with the lumen. A conduit having first and second ends and a passageway extending therethrough is also provided. The conduit is axially aligned with the introducer needle. The first end of the conduit is connected to the fitting such that the conduit passageway is in fluid communication with the second passageway. The conduit and the introducer needle are axially aligned. A guide wire penetrable seal assembly is connected to the second end of the conduit in fluid communication with the conduit passageway for preventing the passage of fluid from within the conduit and air from outside the conduit, and for introduction of the guide wire into the conduit.

In another aspect, the present invention provides a catheter guide wire introducing device for aspiration of a body part and insertion of a guide wire into the body part. The catheter guide wire introducing device includes a flexible bulb having a first end, a second end and an interior cavity. A fitting is located on the first end of the flexible bulb. The fitting includes a chamber. An introducer needle having first and second ends and a lumen is provided, with the first end of the needle being connected to the fitting such that the lumen is in fluid communication with the chamber. A conduit is provided having first and second ends and a passageway extending therethrough. The conduit is axially aligned with the introducer needle, and the first end of the conduit is connected to the fitting such that the conduit passageway is in fluid communication with the chamber. A guide wire penetrable seal assembly is connected to the second end of the conduit in fluid communication with the conduit passageway for preventing the passage of fluid from within the conduit and air from outside the conduit therethrough, and for introduction of a guide wire into the conduit.

In another aspect, the present invention provides a method for using an introducer device for aspirating and inserting a guide wire into a body part. The device includes (i) a flexible bulb having a first end, a closed second end and an interior cavity, (ii) a fitting located on the first end of the bulb, the fitting including an internal chamber and first and second axially aligned passageways in fluid communication with the chamber, and a third passageway in fluid communication between the chamber and the internal cavity of the flexible bulb; (iii) an introducer needle having first and second ends and a lumen, the first end of the needle being connected to the fitting such that the first passageway is in fluid communication with the lumen; (iv) a conduit having first and second ends and a passageway extending therethrough, the conduit being axially aligned with the introducer needle, the first end of the conduit being connected to the fitting such that the conduit passageway is in fluid communication with the second passageway, with the conduit and the introducer needle being axially aligned; and (v) a guide wire penetrable seal assembly connected to the second end of the conduit in fluid communication with the conduit passageway for preventing the passage of fluid from within the conduit and air from outside the conduit therethrough and for introduction of the guide wire into the conduit. The method comprises the steps of:

(a) depressing the flexible bulb to evacuate the flexible bulb through the channel and the needle;
(b) introducing the needle into a body part;
(c) releasing the flexible bulb to create a vacuum to draw fluid from the body part into the bulb and aspirate the body part;
(d) inserting a guide wire through the guide wire penetrable seal assembly; and
(e) sliding the guide wire through the chamber and the lumen of the needle and into the body part.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is an elevational view showing a catheter guide wire introducing device in accordance with the present invention introducing a guide wire into a body part.

FIG. 2 is a cross-sectional view of the catheter guide wire introducing device, partially disassembled, taken along lines 2—2 in FIG. 1;

FIG. 3 is a cross-sectional view showing the assembled bi-directional valve taken from the area indicated in FIG. 2;

FIG. 4 is an elevational view taken along lines 4—4 in FIG. 2;

DETAILED DESCRIPTION OF THE INVENTION

Figure 6:
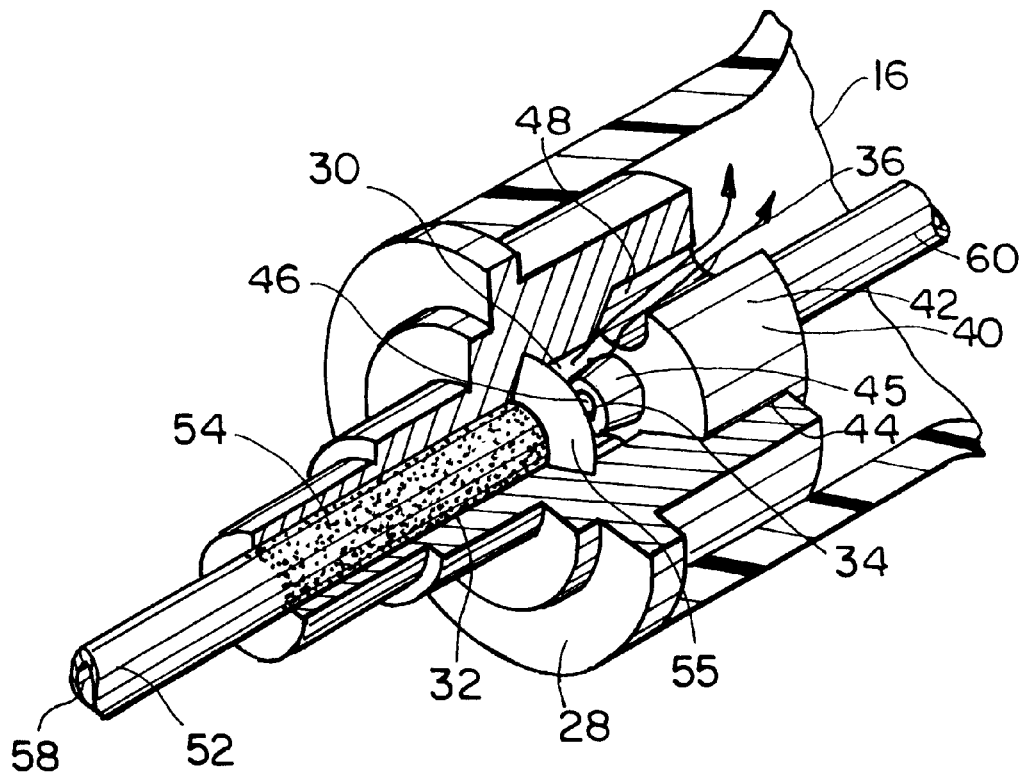
FIG. 6 is an enlarged perspective view, partially broken away, of the fitting located at the first end of the catheter guide wire introducing device illustrating the flow path into the flexible bulb.
Figure 5:
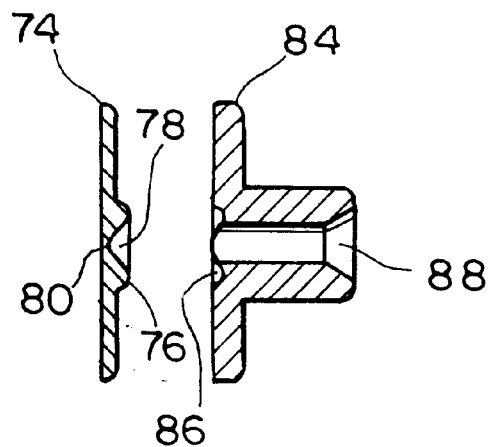
FIG. 5 is an enlarged view of the seal and the seal support of the catheter guide wire introducing device shown in FIG. 2.

Certain terminology is used herein for convenience only and is not be taken as a limitation on the present invention. The words "right," "left," "outwardly" and "inwardly" designate directions in the drawings to which reference is made. The words "distal" and "proximal" refer to directions closer to and away from, respectively, the "needle" or "insertion end" of the catheter guide wire introducing device in accordance with the present invention. The terminology includes the words above specifically mentioned, derivatives thereof, and words of similar import.

The following describes preferred embodiments of the invention. However, it should be understood, based on this disclosure, that the invention is not limited by the preferred embodiments described herein. Referring now to the drawings, wherein like numbers are used to designate the same elements throughout, there is shown in FIGS. 1 through 6 a preferred embodiment of a catheter guide wire introducing device 10 for aspiration of a body part, such as a blood vessel 12 (shown in phantom lines in FIG. 1), and insertion of a guide wire 14 into the body part 12. The guide wire may be straight or have a J-shaped insertion end, as shown in FIG. 1, to prevent the end of the guide wire 14 from catching on the inner wall of the blood vessel 12.

As shown in FIGS. 1 and 2, a flexible bulb 16 having a first end 18, a second end 20 and an interior cavity 22 is provided. Preferably, the flexible bulb 16 is made of a polymeric material, and more preferably of a clear polymeric material such as 1064 PVC. However, it will be recognized by those skilled in the art from the present disclosure that other suitable materials, which are preferably medical grade, can be used, if desired.

Referring now to FIGS. 1, 2 and 6, a fitting 28 is located on the first end 18 of the flexible bulb 16. The fitting 28 includes an internal chamber 30, best shown in FIG. 6, and first and second axially aligned passageways 32, 34 in fluid communication with the chamber 30. A third passageway 36 is provide in the fitting 28 in fluid communication between the chamber 30 and the interior cavity 22 of the flexible bulb 16.

Preferably, the fitting 28 is made of a medical grade polymeric material, such as USP class VI ABS. However, it will be recognized by those skilled in the art from the present disclosure that other types of polymeric or metallic materials may be used, if desired.

Referring again to FIGS. 1 and 2, an introducer needle 52 having first and second ends 54, 56 and a lumen 58 is provided. The first end 54 of the needle 52 is connected to the fitting 28 in first passageway 32 such that at least the end of the first passageway 32 adjacent to the internal chamber 30 is in fluid communication with the lumen 58, depending upon the location of the first end 54 of the needle 52 in the first passageway 32. The first end 54 of the needle 52 preferably includes a roughened surface to allow a more secure connection to the fitting 28. The second end 56 of the needle 52 is sharpened to allow for penetration of a blood vessel 12, as shown in FIG. 1.

As shown in detail in FIG. 6, a funnel 55 is preferably located on the first end 54 of the needle 52 to ensure that the guide wire 14 can be passed through the internal chamber 30 from axial bore 46 in the plug 40 and into the lumen 58 of the needle 52. This is especially important for the insertion of a guide wire 14 having a J-shaped end which must be temporarily straightened prior to introduction into the catheter guide wire introducing device 10. The J-shaped end has a tendency to try to return to its "J" shape as it passes through the internal chamber 30, and the funnel 55 guides the end of the guide wire 14 into the first end 54 of the needle lumen 58. It will be recognized by those skilled in the art that the funnel 55 need not be part of the needle 52, but may be formed as part of the fitting 28 in proximity to the first end 54 of the needle 52, or may be formed as a combination of both.

In the preferred embodiment, the needle 52 is preferably made of 303 stainless steel and has an outside diameter of approximately 0.050 inches and an inside diameter of approximately 0.042 inches. However, it will be recognized by those skilled in the art from the present disclosure that the needle 52 may be made from other suitable materials and may have a different size to suit a particular application.

As shown in detail in FIGS. 2 and 6, a plug 40 having an outer surface 42 is seated within an opening 44 defined by an interior wall of the fitting 28 generally opposite to the first passageway 32. The second passageway 34 is defined by an axial bore 46 through the plug 40, and the chamber 30 is located between the plug 40 and the first passageway 32. The third passageway 36 extends longitudinally between the plug 40 and the interior wall of the fitting 28, and is preferably formed by at least one channel 48 located on the periphery of the plug 40. Preferably, at least two channels 48, 50 are provided and additional channels may be added, if desired. The plug 6 is preferably made of a class 6 medical grade ABS.

Still with reference to FIG. 6, preferably the plug 40 includes a tapered portion 45 which extends into the internal chamber 30. The spacing between the tapered portion 45 of the plug 40 and the funnel 55 is preferably set to a distance which does not allow the end of the guide wire 14, as described above, to return to its "J" shape in the internal chamber 30. It will be recognized by those skilled in the art that this spacing will vary depending on the size of the "J" at the end of the guide wire 14, which is generally a function of the guide wire diameter, and can varied as needed. Preferably, the combination of the spacing between the tapered portion 45 and the funnel 55, along with the shape of the funnel 55, allows the guide wire 14 to pass through the internal chamber 30 without unbending.

Referring now to FIG. 2, a conduit 60 having first and second ends 62, 64 and a passageway 66 extending therethrough is provided. The conduit 60 is axially aligned with the introducer needle 52, with the first end of the conduit 60 being connected to the fitting 28, preferably by forming the conduit integrally with the plug 40. However, the conduit 60 may also be provided as a separate piece which is molded together with the plug 40 or joined to the plug 40 in a secondary operation such that the conduit passageway 66 is in fluid communication with the second passageway 34 and the internal chamber 30. The conduit 60 is preferably located within the flexible bulb 16 and extends from the fitting 28 at the first end of the flexible bulb to the second end 20 of the flexible bulb 16.

Referring now to FIGS. 1–5, a guide wire penetrable seal assembly 70 is connected to the second end 64 of the conduit and is in fluid communication with the conduit passageway 66 for preventing the passage of fluid within the conduit 60 outside the device 10, such as blood received in the conduit 60 during aspiration of a blood vessel 12, and for introducing the guide wire 14 into the conduit 60. The seal assembly 70 includes a seal support body 72 which is located at the second end 20 of the flexible bulb 16 and seals the interior cavity 22 at the second end 20 of the flexible bulb 16.

The seal support body 72 is preferably formed integrally with the conduit 60 and the plug 40. However, the seal support body 72 may be formed as a separate piece which is then connected to the second end 64 of the conduit 60, if desired. The seal support body 72 is preferably made of a polymeric material, such as a medical grade ABS. However, it will be recognized by those skilled in the art from the present disclosure that the seal support body 72 can be made of other suitable polymeric or metallic materials, such as stainless steel, if desired.

Referring now to FIGS. 2–5, preferably the guide wire penetrable seal assembly 70 includes a seal 74 with a central raised portion 76. The raised portion includes a depression 78, with a slit 80 being located in the depression 78 which is generally in alignment with the conduit 60. The slit 80 may be normal to the surface to the seal 74 or more preferably is at an acute angle relative to the surface of the seal 74, if desired.

The seal 74 is preferably made from a medical grade natural or synthetic rubber, or an elastomeric material. In the preferred embodiment, the seal 74 is made of KRATON™ which is a thermoplastic elastomer available from Shell Chemical Co. or GLS Plastics.

A seal support 84 is located adjacent to the raised portion 76 of the seal 74. The seal support 84 includes a complementary surface 86 to the central raised portion 76 and the depression 78 of the seal 74, and also includes a central opening 88 defined therethrough. The seal support body 72 includes a cylindrical recess 73 which receives the seal 74 and the seal support 84. The complementary surface 86 on the seal support 84 prevents the seal 74 from deforming in the area of the depression 78 and the slit 80 when pressure is applied from within the conduit passageway 66 to the seal 74 in order to prevent material from within the interior cavity 22 of the flexible bulb 16 or the conduit 60 from passing out through the seal 74. The shape of the complementary surface 86 on the seal support 84 also prevents deflection of the seal due to negative (vacuum) pressure from within the conduit 60 or flexible bulb 16 which could result in the introduction of outside air.

However, the guide wire 14 can be introduced through the slit 80 in the seal 74 with minimal resistance. The guide wire 14 physically displaces the seal 74 in the area of the slit 80 in order to pass through the slit 80 and enter the conduit 60. The seal 74 conforms to the shape of the guide wire 14 to substantially prevent the entry of outside air along with the guide wire 14.

A cap 90 is provided to hold the seal 74 and the seal support 84 within the cylinder recess 73 of the seal support body 72. The cap 90 includes a conical recessed opening 92 and an axial bore 94 extending therethrough which are adapted to direct the guide wire 14 to the slit 80 in the seal 74.

Preferably, the first end 18 of the flexible bulb 16 is affixed to the fitting 28 and the second end 20 of the flexible bulb is affixed to seal valve support body 72. In the preferred embodiment, the bonds are made with an adhesive, such as LOCTITE 3301. However, other suitable adhesives can be used, if desired, depending upon the materials being used.

Referring again to FIG. 1, the introducer device 10 is preferably used for aspirating and inserting a guide wire 14 into a body part, such as the blood vessel 12 shown in FIG. 1. Preferably, the bulb 16 is first filled with a heparinized saline solution and then emptied by squeezing or depressing the bulb 16 together between the user's fingers. This evacuates air and the saline solution from the flexible bulb 16 out through the channels 48, the chamber 30 and the needle 52. While maintaining the bulb compressed, the needle 52 is introduced into the body part, which may be any body part. However, for the present description reference will be made to the blood vessel 12, as shown in FIG. 1. The flexible bulb 16 is released as the needle 52 is advanced. The blood vessel 12 is aspirated by piercing with the needle 52, with the vacuum created by releasing the flexible bulb 16 drawing blood from the vessel 12 through the lumen 58 of the needle 52, the internal chamber 30, the channels 48 and into the bulb 16. This allows the physician to ensure that the body part, such as blood vessel 12 has been properly located, even in situations where flashback flow is not expected, such as venous catheterization.

The bulb 16 requires only one hand to operate in order to create and release the suction force, as opposed to a standard aspirating syringe which requires two hands to manipulate in order to draw blood into the syringe. This allows the physician or other user to control the drawing of blood with one hand while providing for collection of the flashback in the flexible bulb 16.

The guide wire 14 is inserted through the seal assembly 70 and is slid through the passageway 66 in the conduit 60, the internal chamber 30 in the fitting 28, and the lumen 58 of the introducer needle 52 and into the blood vessel 12. The introducing device 10 can then be removed from the blood vessel 12 over the guide wire 14 while leaving the guide wire 14 in the vessel 12. The procedure for catheterization can then be carried out by inserting the catheter over the guide wire 14 or using the guide wire 14 as a guide for catheterization by any one of the known methods.

It is also possible to use the present introducing device 10 for direct insertion of a catheter by placing a catheter (not shown) over the needle 52 such that the second end 56 of the needle 52 extends beyond the catheter tip. The body part 12 is aspirated using the introducing device 10 as described above. Once the needle 52 is properly positioned within the body part, such as the blood vessel 12, the catheter is advanced over the needle 52 and into position.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A catheter guide wire introducing device for aspiration of a body part and insertion of a guide wire into the body part comprising:

a flexible bulb having a first end, a second end and an interior cavity;

a fitting located on the first end of the flexible bulb, the fitting including an internal chamber and first and second axially aligned passageways in fluid communication with the chamber, and a third passageway in fluid communication between the chamber and the interior cavity of the flexible bulb;

an introducer needle having first and second ends and a lumen, the first end of the needle being connected to the fitting such that the first passageway is in fluid communication with the lumen;

a conduit having first and second ends and a passageway extending therethrough, the conduit being axially aligned with the introducer needle, the first end of the conduit being connected to the fitting such that the conduit passageway is in fluid communication with the second passageway; and a guide wire penetrable seal assembly connected to the second end of the conduit in fluid communication with the conduit passageway for preventing the passage of fluid from within the conduit and air from outside the conduit therethrough, and for introduction of a guide wire into the conduit, wherein the guide wire penetrable seal assembly comprises a seal having a surface and a seal support adjacent to the seal, the seal support having a surface complementary to the surface of the seal such that the surface of the seal and the surface of the seal support are in facing engagement and the seal is capable of aspirating a body part.

2. The device of claim 1 wherein the conduit is located within the flexible bulb and extends from the fitting at the first end of the flexible bulb to the second end of the flexible bulb, a seal support body being located at the second end of the flexible bulb which seals the interior cavity at the second end of the flexible bulb and connects the second end of the conduit to the guide wire penetrable seal assembly.

3. The device of claim 2 wherein the seal has a central raised portion having a depression located at an apex of the raised portion, an angular slit being located in the depression which is generally in alignment with the conduit, and the seal support has a central opening, wherein the seal support body includes a cylindrical recess which receives the seal and the seal support.

4. The device of claim 3 further comprising a cap which holds the seal and the seal support within the cylindrical recess, the cap including a conical recessed opening and an axial bore extending therethrough adapted to direct the guide wire to the slit in the seal.

5. The device of claim 2 wherein the first end of the flexible bulb is affixed to the fitting and the second end of the flexible bulb is bonded to the seal support body.

6. The device of claim 1 wherein the flexible bulb comprises a clear polymeric material.

7. The device of claim 1 wherein the flexible bulb comprises a clear elastomeric material.

8. A catheter guide wire introducing device for aspiration of a body part and insertion of a guide wire into the body part comprising:

a flexible bulb having a first end, a second end and an interior cavity;

a fitting located on the first end of the flexible bulb the fitting including an internal chamber and first and second axially aligned passageways in fluid communication with the chamber, and a third passageway in fluid communication between the chamber and the interior cavity of the flexible bulb, the fitting including a plug having an outer surface seated within an opening defined by an interior wall of the fitting opposite to the first passageway, the second passageway being defined by an axial bore through the plug, and the third passageway extending longitudinally between the plug and the interior wall of the fitting;

an introducer needle having first and second ends and a lumen, the first end of the needle being connected to the fitting such that the first passageway is in fluid communication with the lumen;

a conduit having first and second ends and a passageway extending therethrough the conduit being axially aligned with the introducer needle, the first end of the conduit being connected to the fitting such that the conduit passageway is in fluid communication with the second passageway; and a guide wire penetrable seal assembly connected to the second end of the conduit in fluid communication with the conduit passageway for preventing the passage of fluid from within the conduit and air from outside the conduit therethrough, and for introduction of a guide wire into the conduit.

9. A catheter guide wire introducing device for aspiration of a body part and insertion of a guide wire into the body part comprising:

a flexible bulb having a first end, a second end and an interior cavity;

a fitting located on the first end of the flexible bulb, the fitting including a chamber;

an introducer needle having first and second ends and a lumen, the first end of the needle being connected to the fitting such that the lumen is in fluid communication with the chamber;

a conduit having first and second ends and a passageway extending therethrough, the conduit being axially aligned with the introducer needle, the first end of the conduit being connected to the fitting such that the conduit passageway is in fluid communication with the chamber; and a guide wire penetrable seal assembly connected to the second end of the conduit in fluid communication with the conduit passageway for preventing the passage of fluid from within the conduit and air from outside the conduit therethrough, and for introduction of a guide wire into the conduit, wherein the guidewire penetrable seal assembly comprises a seal having a surface and a seal support adjacent to the seal, the seal support having a surface in facing engagement with the surface of the seal and being capable of aspirating a body part.

10. The device of claim 9 wherein the conduit is located within the flexible bulb and extends from the fitting at the first end of the flexible bulb to the second end of the flexible bulb, a seal support body being located at the second end of the flexible bulb which seals the interior cavity at the second end of the flexible bulb and connects the second end of the conduit to the guide wire penetrable seal assembly.

11. The device of claim 9 wherein the guide wire penetrable seal assembly comprises a seal with a central raised portion having a depression located at an apex of the raised portion, an angular slit being located in the depression which is generally in alignment with the conduit, a seal support being located adjacent to the raised portion and having a complementary surface to the seal and a central opening, wherein the seal support body includes a cylindrical recess which receives the seal and the seal support.

12. The device of claim 11 further comprising a cap which holds the seal and the seal support within the cylindrical recess, the cap including a conical recessed opening and an axial bore extending therethrough adapted to direct the guide wire to the slit in the seal.

13. A catheter guide wire introducing device for aspiration of a body part and insertion of a guide wire into the body part comprising:

a flexible bulb having a first end, a second end and an interior cavity;

a fitting located on the first end on the flexible bulb, the fitting including a chamber;

an introducer needle having first and second ends and a lumen, the first end of the needle being connected to the fitting such that the lumen is in fluid communication with the chamber;

a conduit having first and second ends and a passageway extending therethrough, the conduit being axially aligned with the introducer needle, the first end of the conduit being connected to the fitting such that the conduit passageway is in fluid communication with the chamber; and a guide wire penetrable seal assembly connected to the second end of the conduit in fluid communication with the conduit passageway for preventing the passage of fluid from within the conduit and air from outside the conduit therethrough, and for introduction of a guide wire into the conduit, wherein the guide wire penetrable seal assembly comprises a seal having a surface with a central raised portion having a depression located at an apex of the raised portion, a slit being located in the depression which is generally an alignment with the conduit, and a seal support adjacent to the seal, the seal support having a surface complementary to the surface of the seal, wherein the surface of the seal support comprises a corresponding central depression which facially engages the central raised portion of the seal and wherein the seal is capable of aspirating a body part.

14. A method for using an introducer device for aspirating and inserting a guide wire into a body part, the device including: (i) a flexible bulb having a first end, a second end and an interior cavity; (ii) a fitting located on the first end of the flexible bulb, the fitting including an internal chamber and first and second axially aligned passageways in fluid communication with the chamber, and a third passageway in fluid communication between the chamber and the interior cavity of the flexible bulb; (iii) an introducer needle having first and second ends and a lumen, the first end of the needle being connected to the fitting such that the first passageway is in fluid communication with the lumen; (iv) a conduit having first and second ends and a passageway extending therethrough, the conduit being axially aligned with the introducer needle, the first end of the conduit being connected to the fitting such that the conduit passageway is in fluid communication with the second passageway, with the conduit and the introducer needle being axially aligned; and (v) a guide wire penetrable seal assembly connected to the second end of the conduit in fluid communication with the conduit passageway for preventing the passage of fluid from within the conduit and air from outside the conduit therethrough and for introduction of the guide wire into the conduit, the method comprising the steps of:

(a) depressing the flexible bulb to evacuate the flexible bulb through the channel and the needle;

(b) introducing the needle into a body part;

(c) releasing the flexible bulb to create a vacuum and draw fluid from the body part into the bulb and aspirate the body part;

(d) inserting a guide wire through the guide wire penetrable seal assembly; and (e) sliding the guide wire through the chamber and the lumen of the needle and into the body part.

15. The method of claim 14 further comprising the step of:

(f) removing the introducing device from the body part over the guide wire while leaving the guide wire in the body part.

16. The method of claim 14 wherein the introducing device is operated for aspirating the body part with one hand.

* * * * *